US008799017B2

(12) United States Patent
Parker et al.

(10) Patent No.: US 8,799,017 B2
(45) Date of Patent: Aug. 5, 2014

(54) APPARATUS AND METHOD FOR MANAGING INTERACTION-BASED SERVICES

(71) Applicants: Marilyn E. Parker, Olathe, KS (US); Abhijit Pandya, Boca Raton, FL (US); Sam Hsu, Boca Raton, FL (US); Shihong Huang, Boca Raton, FL (US)

(72) Inventors: Marilyn E. Parker, Olathe, KS (US); Abhijit Pandya, Boca Raton, FL (US); Sam Hsu, Boca Raton, FL (US); Shihong Huang, Boca Raton, FL (US)

(73) Assignee: Florida Atlantic University, Boca Raton, FL (US)

( * ) Notice: Subject to any disclaimer, the term of this patent is extended or adjusted under 35 U.S.C. 154(b) by 0 days.

(21) Appl. No.: 13/866,615

(22) Filed: Apr. 19, 2013

(65) Prior Publication Data

US 2013/0311203 A1    Nov. 21, 2013

Related U.S. Application Data

(63) Continuation of application No. 12/715,800, filed on Mar. 2, 2010, now abandoned.

(60) Provisional application No. 61/156,763, filed on Mar. 2, 2009.

(51) Int. Cl.
| | | |
|---|---|---|
| G06Q 50/00 | (2012.01) | |
| G06Q 50/24 | (2012.01) | |
| G06Q 10/10 | (2012.01) | |
| G10L 15/26 | (2006.01) | |
| G06F 19/00 | (2011.01) | |
| G06Q 50/22 | (2012.01) | |
| G06Q 10/00 | (2012.01) | |

(52) U.S. Cl.
CPC ............. *G06F 19/322* (2013.01); *G06Q 50/24* (2013.01); *G06Q 10/10* (2013.01); *G10L 15/265* (2013.01); *G06Q 50/22* (2013.01)
USPC .................................................. 705/2; 705/3

(58) Field of Classification Search
USPC ........................................................... 705/2
See application file for complete search history.

(56) References Cited

U.S. PATENT DOCUMENTS

| | | | |
|---|---|---|---|
| 5,583,758 A | 12/1996 | McIlroy et al. | |
| 6,206,829 B1 | 3/2001 | Iliff | |
| 2003/0153819 A1 | 8/2003 | Iliff | |
| 2007/0214013 A1 | 9/2007 | Silverman | |
| 2008/0208629 A1 | 8/2008 | Davison | |
| 2008/0255875 A1* | 10/2008 | Sharda ............................. 705/2 |

OTHER PUBLICATIONS

Choi, MobileNurse: hand-held information system for point of nursing care, 2004, Computer Methods and Programs in Biomedicine, vol. 74, Issue 3, pp. 245-254.*

(Continued)

*Primary Examiner* — Tran Nguyen
(74) *Attorney, Agent, or Firm* — Novak Druce Connolly Bove + Quigg LLP

(57) ABSTRACT

A system that incorporates teachings of the present disclosure may include, for example, a syntactic component for retrieving records corresponding to an individual and analyzing the records to assess a condition for the individual; a user interface for capturing interaction data that is associated with an encounter between the individual and a service provider; and a semantic component for comparing the interaction data to interaction criteria, where an action plan for the individual is generated based at least in part on the assessed condition and the comparison of the interaction data to the interaction criteria. Other embodiments are disclosed.

21 Claims, 19 Drawing Sheets

(56) References Cited

OTHER PUBLICATIONS

International Search Report mailed on Oct. 20, 2010 in PCT Appln. No. PCT/US2010/025892, international filed Mar. 2, 2010. (5 pages).

Non Final Office Action mailed on Jan. 24, 2012 in Appln. No. 12/715,800. (17 pages).
Non Final Office Action mailed on Oct. 24, 2012 in Appln. No. 12/715,800. (15 pages).

* cited by examiner

APPARATUS AND METHOD FOR MANAGING INTERACTION-BASED SERVICES

CROSS-REFERENCE TO RELATED APPLICATION

This patent application claims priority to and the benefit of U.S. patent application Ser. No. 12/715,800, filed Mar. 2, 2010, which is a non-provisional application of U.S. Provisional Patent Application No. 61/156,753, filed Mar. 2, 2009, both of which is are herein incorporated by reference in their entirety.

FIELD OF THE DISCLOSURE

The present disclosure relates generally to services provided to individuals and more specifically to an apparatus and method for managing interaction-based services, such as healthcare.

BACKGROUND

With technology advancements and our ever-increasing knowledge, services provided to individuals, such as nursing and healthcare, have become more complex as well as increasingly expensive. Efforts have been underway to improve such services including the management of healthcare services. These efforts include implementing the use of electronic healthcare records for patients.

Medical care is often perceived as consisting of a physician's diagnosis of the patient and a physician's treatment of the patient. Medical records and the emerging electronic healthcare records are reflective of this perception. However, the amount of time that a physician spends with the patient during the diagnosis and treatment process is often far less than that of the one or more nurses providing care to the patient.

Additionally, medical records and electronic healthcare records document the tested conditions of the patient (vital signs, test results, and so forth) and document the patient's asserted condition (pain, discomfort, and so forth). These records may include actions taken with respect to the patient, such as when medication was dispensed. However, the contemporary records fail to fully capture neither the condition of the patient, nor the nursing care provided.

A need therefore arises for a system and method of effectively managing services provided to individuals, including both the nursing and healthcare provided. There is a further need for a system and method to more fully capture and understand the condition of the individual, including progress toward desired healthcare outcomes. There is yet a further need for a system and method that generates or adjusts a healthcare model associated with the patient based on patient and nursing relationships, and captures and manages nursing practice.

SUMMARY

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In one embodiment of the present disclosure, a storage medium for healthcare can include computer instructions for: retrieving medical records corresponding to a patient; analyzing the medical records to assess a health risk for the patient; receiving interaction data through a user interface, the interaction data being associated with an encounter between the patient and a nurse; comparing the interaction data to interaction criteria; and determining a healthcare plan for the patient based at least in part on the assessed health risk and the comparison of the interaction data to the interaction criteria.

In another embodiment of the present disclosure, a management system can include a syntactic component for retrieving records corresponding to an individual and analyzing the records to assess a condition for the individual; a user interface for capturing interaction data that is associated with an encounter between the individual and a service provider; and a semantic component for comparing the interaction data to interaction criteria, where an action plan for the individual is generated based at least in part on the assessed condition and the comparison of the interaction data to the interaction criteria.

In another embodiment of the present disclosure, a method for managing healthcare can include receiving interaction data through a user interface of a processor, the interaction data being associated with an encounter between a patient and a nurse; comparing the interaction data to interaction criteria by applying a natural language process of the processor; visualization of the progress of nurses and patient encounter, and determining a healthcare plan for the patient based at least in part on the comparison of the interaction data to the interaction criteria using the processor.

BRIEF DESCRIPTION OF THE DRAWINGS

FIG. 6 depicts a graphical user interface for one or more of the embodiments of FIGS. 1-5;

Figure 14:
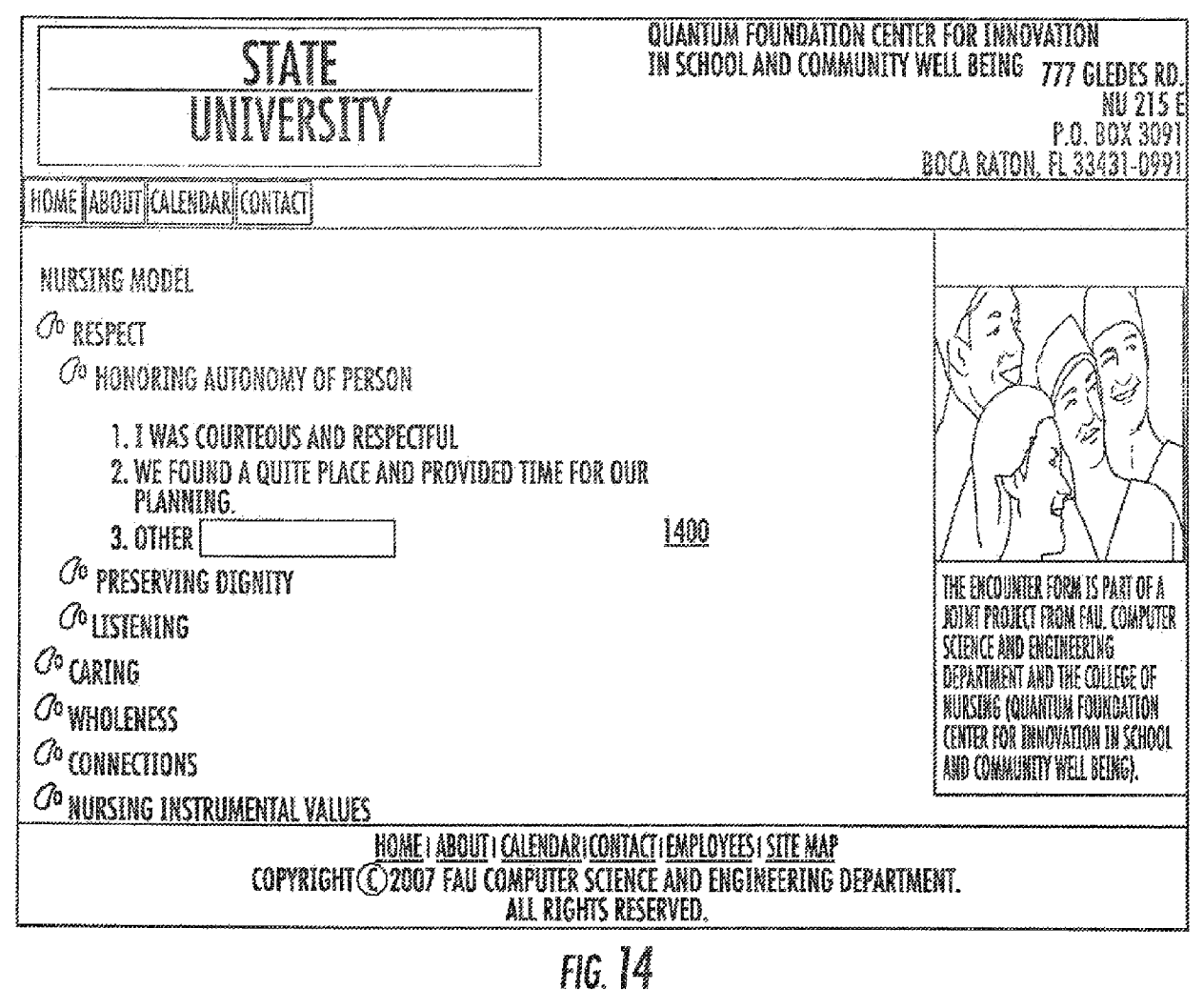

FIG. 14 depicts a graphical user interface for one or more of the embodiments of FIGS. 1-9B;

DETAILED DESCRIPTION

Figure 1:
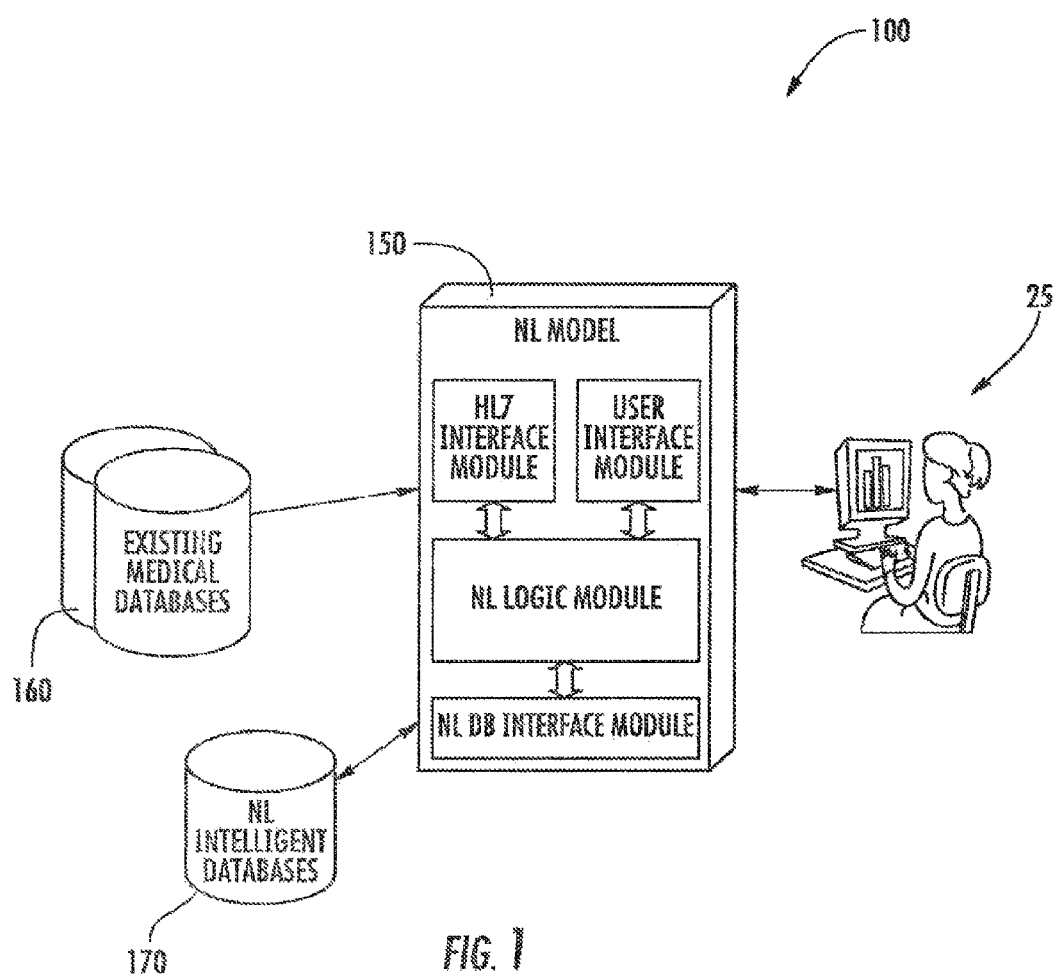
FIG. 1 depicts an exemplary embodiment of a system for providing healthcare or wellness, including the integration of nursing practice into the existing healthcare systems.
Figure 2:
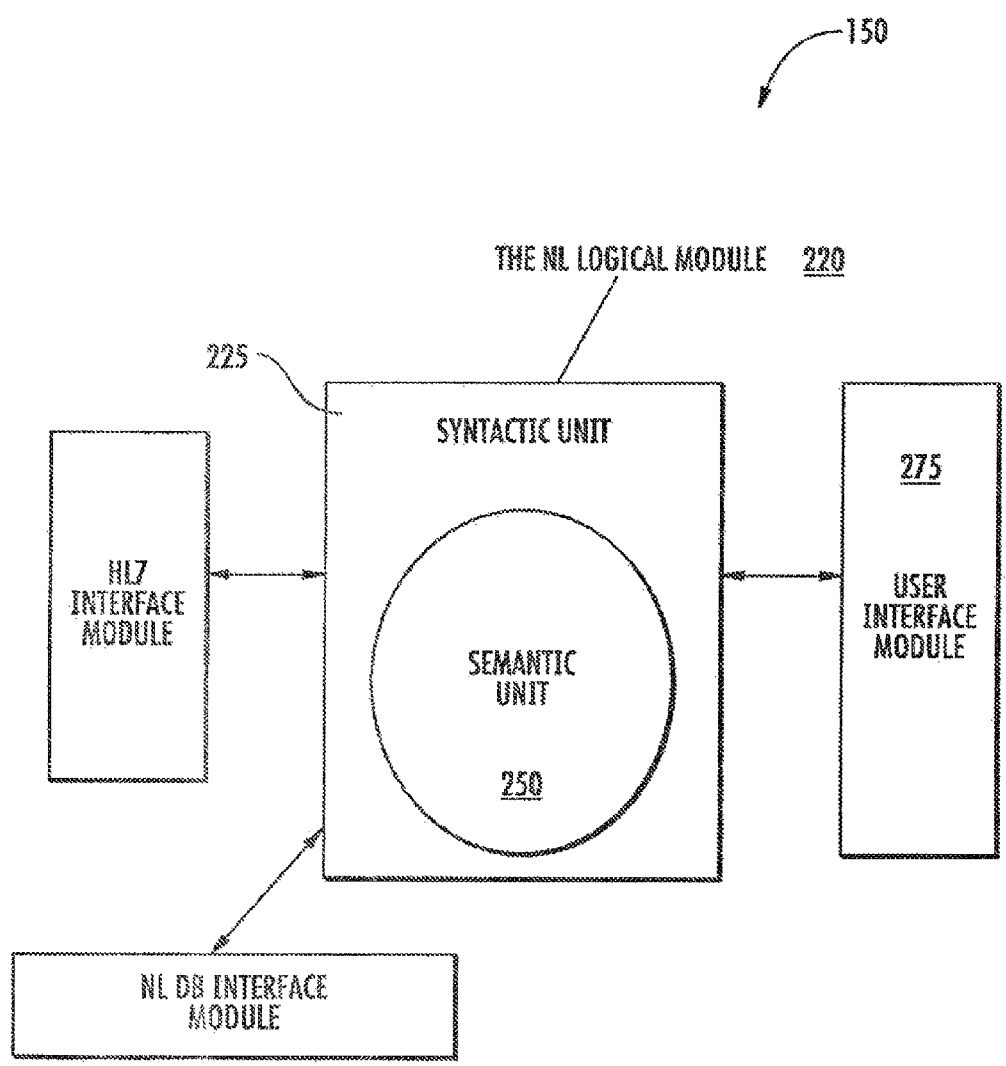
FIG. 2 depicts an exemplary embodiment of a nursing language model operable with the system of FIG. 1.
Figure 3:
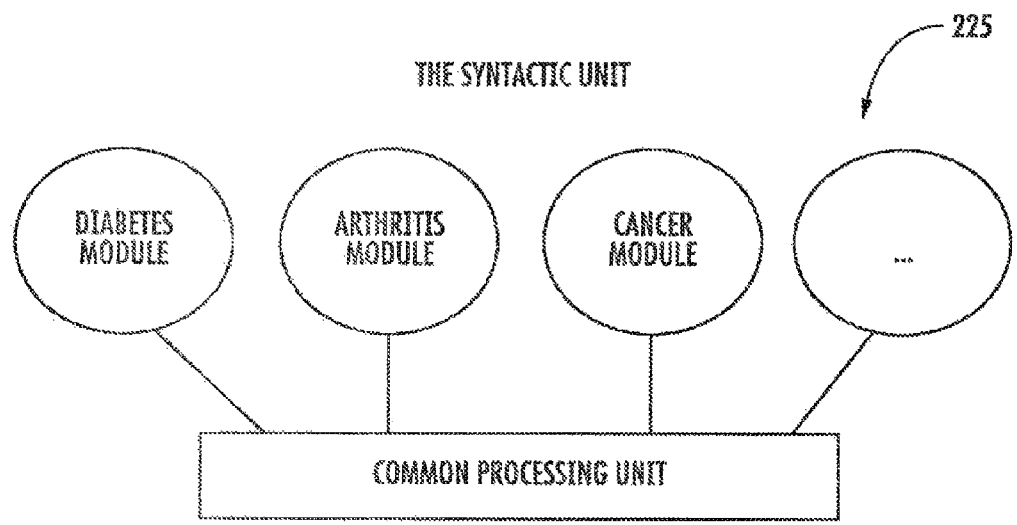
FIG. 3 depicts an exemplary embodiment of a syntactic unit operable with the module of FIG. 2.

The exemplary embodiments described herein are directed towards providing personal services to individuals and/or groups, including providing healthcare and/or wellness. While the exemplary embodiments are described with respect to medical care including nursing practice, the present disclosure contemplates the embodiments described herein being applicable to other environments and/or services, including services provided by emergency medical technicians, psychologists, social workers, first responders and so forth. The present disclosure also contemplates the services being other than wellness, such as where the discipline involves identifiable subject matter (including recognizable terms, grammar and the like) and is dependent on social context and interaction, such as business relationships, law enforcement, education and so forth In one or more of the exemplary embodiments, nursing knowledge, which is information or data associated with the interaction of the nurses and the patients, is collected.

For example, the exemplary embodiments can capture the expressions of the synergy between the nurses and the patients. In one embodiment, the synergy can be based on determined factors from information gathered during the interaction in addition to the use of traditionally documented data, such as vital signs, test results, and patient's asserted complaints. For instance, information provided by the patient unrelated to the patient's condition can be analyzed to determine the synergy, which can then be utilized for determining the accuracy of information provided by the patient. The data can then be analyzed by the nurses and classified using their knowledge according to nursing theory In one or more of the exemplary embodiment, the interaction between the nurses and the patient is captured and effectively analyzed for improving the resulting healthcare provided to the patient. The exemplary embodiments can also capture and analyze interaction between other individuals associated with the patient, such as gathering data from the encounter between the nurse and family members and/or the family members and the patient The exemplary embodiments provide for the information captured or otherwise generated to be used for modeling or improving the model for the healthcare of a patient. The model can be of the patient and/or can be for the healthcare to be provided to the patient. In one embodiment, computational analysis can be employed for extracting the appropriate representation of the aspects relevant to health records from an encounter between a nurse and a patient. For instance, the exemplary embodiment can provide for the aspects of care provided by a nurse(s) to be more tractable. These aspects can include health related information gained through the nurse offering presence, providing respect, establishing connectedness, and so forth. In one embodiment, the model can emulate how a nurse relates extracted health data to the nurse's knowledge data repository and can influence the health outcome of the patient leading to diagnosis and/or treatment.

In another embodiment, the system can interface with, and complement, other medical-based electronic record systems. The system can have advantages beyond improving healthcare of the patients, such as where the communication of distinctive nursing practice can yield data for knowledge generation, enhance the value of nursing, and improve satisfaction and retention of nurses in various practice settings.

Figure 4:
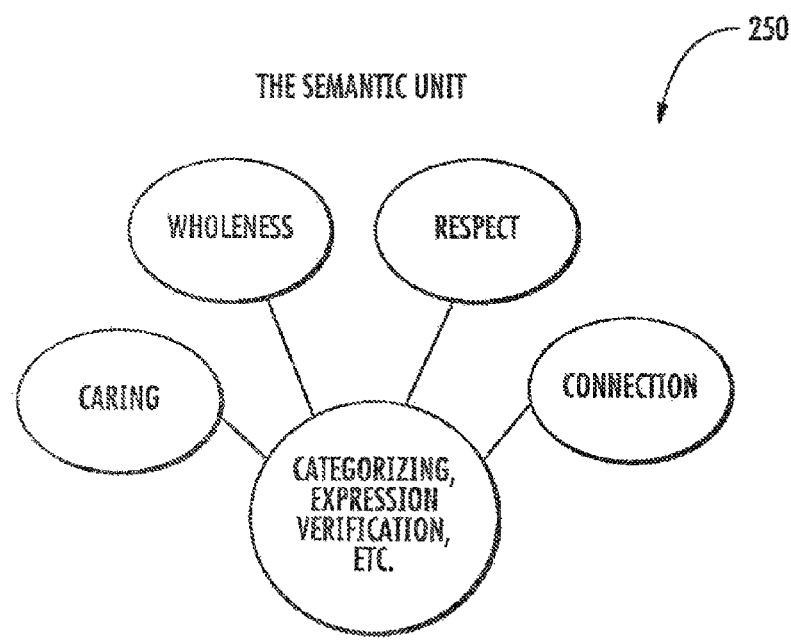
FIG. 4 depicts an exemplary embodiment of both syntactic and semantic units operable with the module of FIG. 2.
Figure 5:
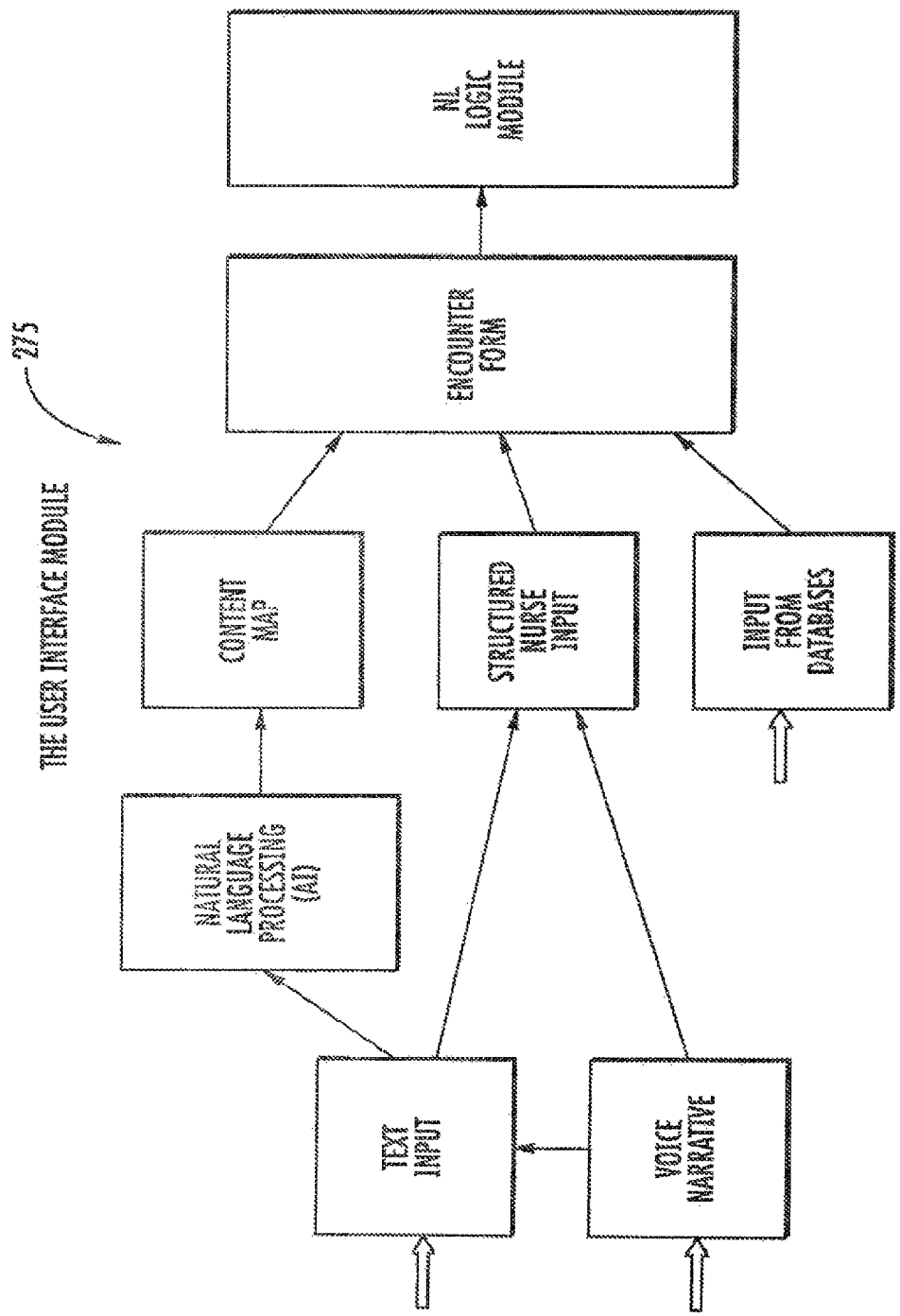
FIG. 5 depicts an exemplary embodiment of a system user interface module operable with the module of FIG. 2.

FIGS. 1-5 depict an exemplary embodiment of a system 100 for capturing nursing knowledge and providing healthcare to a patient. System 100 can include a nursing language device 150 that is communicatively linked to one or more medical databases 160 and one or more language databases 170. The particular number and configuration of the databases 160, 170 can vary and can be in centralized or de-centralized systems. The device 150 can include software being utilized by one or more processors. The device 150 can be accessible by a nurse 25 (or other caregiver such as a Certified Nursing Assistance and so forth) such as through use of the user interface module 275. The particular mode of interface for module 275 can vary and can be combinations of interfacing including text and speech input as shown in FIG. 5, as well as remote input through a nurse's PDA or the like.

The device 150 can include a natural language logic module 220 with a quantitative or syntactic component 225 and a qualitative or semantic component 250. The syntactic and semantic components 225, 250 can be separate sub-devices and/or separate software, or can be a single software or integrated with device 150. The syntactic component 225 can collect patient data, organize the data, and store the data. The syntactic component 225 can perform quantitative analysis of the data collected. In one embodiment, the syntactic component 225 can analyze health screening data to determine health risk for a patient. The syntactic component 225 can include a processing unit and various modules (see FIG. 3) that correspond to different health concerns. The syntactic component 225 can obtain the patient's existing health records and can utilizes the various modules to assess the patient's risk in various health concerns. For instance, the syntactic component 225 can include a diabetes module, an arthritis module and a cancer module for assessing health risk based on patient data that is retrieved from the medical databases 160 and/or a current medical history.

In one embodiment, the syntactic component 225 can utilize a medical record interface, such as a Health Level 7 compliant module (e.g., based on an ANSI standard body for clinical and administrative data), for retrieving a patient's medical records or otherwise accessing the medical information of the patient.

The particular modules that are utilized by the syntactic component 225 can vary depending on a number of factors, including the age, gender, or other characteristics of the patient. The types of modules utilized by the syntactic component 225 can also vary based on factors that are not associated with the particular patient, such as geography (e.g., medical conditions more prevalent in certain areas), changes to overall health statistics for the population (e.g., a rise in the number of patients being diagnosed with a particular medical condition) and so forth. In one embodiment, the selection of the modules to be utilized by the syntactic component 225 can be based on user input, such as the physician.

In another embodiment, the selection of the modules to be utilized by the syntactic component 225 can be based on an accuracy prediction. For instance, system 100 can compile data associated with the use of various types of modules provided by component 225 when various symptoms are known for a group of patients and based on that data, the system can determine that certain modules are less accurate in their analysis because of a particular group of symptoms. Other criteria can also be used to determine whether one or more of the modules can be excluded or included by the syntactic component 225 in the analysis of the patient's health risk, such as probability of false positives for a certain medical condition, processing resources, and so forth. In one embodiment, the syntactic component 225 can then forward the assessment to the semantic component 250 for further processing and/or directly present the output, such as to the patient, the nurse and/or the physician. The presentation can be performed in a number of ways, including through use of a display device of the system 100 and remotely through use of a PDA or the like.

The semantic component 250 can be applied to any of the components in the syntactic unit 225. Component 250 receives as input the assessment results from the syntactic component 225, as well as data or information associated with the interactions between the nurse and the patient. For example, the interaction data received or otherwise obtained by the semantic component 250 can include the patient's expression of needs, the nurse's expression of caring for the patient and the patient's response, and so forth. The semantic component 250 can include a plurality of modules that are each associated with categories of interaction, such as caring, wholeness, respect and connection as shown in FIG. 4. The interaction data can be analyzed by the corresponding module(s) for further processing to derive a recommendation, which can be a health care treatment plan, an alerting message, and so forth that is suitable to the patient's current situation.

The semantic component 250 allows the system 100 to account for or otherwise analyze caring as a component of nursing. The semantic component 250 can provide for interpreting data that is processed in a proactive manner to provide a better care of patients. The particular form of the input can vary as shown in FIG. 5 and the source of the input can vary as well including the patient, the nurse, and both. In one embodiment, family members or other individuals the interact with the patient can be the source of the interaction data.

In another embodiment, the number or breadth of interacting individuals being used as a source of the interacting data can be analyzed and utilized for determining the healthcare to be provided to the patient. For instance, an accuracy assessment can be made where interaction data from multiple sources (friends, family members, etc.) is weighted more heavily than interaction data from a single source. As another example, the type of source can also be considered in the evaluation. For instance, interaction data from a parent or other individual with a close relationship to the patient can be weighted more heavily than interaction data from someone with a tangential relationship to the patient. Other characteristics of the source can also be used as factors in the analysis of the interaction data including the education level of the source and so forth.

Figure 8:
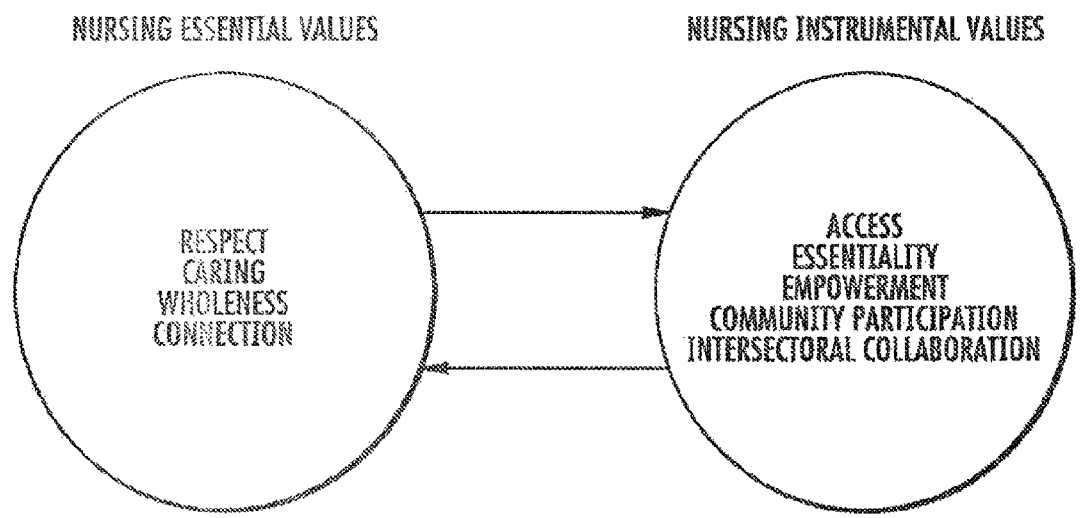
FIG. 8 depicts the bi-directional natures between the nursing essential values and instrumental values, which are the fundamental nursing data values cherished and valued by nurses in their nursing practice.

In one embodiment, the semantic component 250 can utilize interaction data that is based on nursing essential values and nursing instrumental values as shown in FIG. 8. The nursing essential values can be those values that do not change over time, and are essentially and consistently present in nursing practice, education, scholarship and policy. The nursing essential values can include respect, caring, wholeness and connections. The nursing instrumental values can be those values that are necessary for the essential nursing values to be actualized in nursing practice, education, scholarship and policy. The nursing essential values can be based on and interconnected with the nursing essential values and can provide focus for nursing and health care. The nursing essential values can include access, essentiality, empowerment, community participation and intersectoral collaboration. A bidirectional relationship can exist between the nursing essential values and the nursing instrumental values.

Device 150 and semantic component 250 can employ various techniques for recognizing and analyzing inputs, which may be in various forms including text and speech. In one embodiment, a natural-language speech enabled system can be utilized that attempts to closely emulate human-human interaction and ideally allow users to speak in a natural manner, such as through open ended statements. In one embodiment, device 150 and semantic component 250 can include, or otherwise have access to, a relatively large vocabulary and a relatively large grammar, with a high level of natural language understanding in order to understand the free-form response.

In one embodiment, libraries comprising the vocabulary and/or the grammars can be maintained and updated based on utilization of the device 150. For instance, a database of nursing language terms can be built from the interaction data gathered during use of device 150. In another embodiment, the nursing language or interaction terms can be automatically recognized and categorized based on their collection and analysis during a series of interactions between nurses and patients without the intervention of an administrator. In yet another embodiment, the nursing language or interaction terms can be collected and can be reviewed by the administrator or other individual to verify their meaning. Other factors, such as frequency of use and capability of multiple meanings, can be utilized in maintaining the libraries with the terms. For instance, a collected nursing term that is recognized to have multiple, discrete meanings can be categorized as such so that a closer analysis of the context of the term is performed.

In one embodiment, mixed initiative techniques can be utilized with composite grammars which allow slots to be filled arbitrarily. In another embodiment, Natural Language Processing (NLP) can be utilized to parse user text or utterance in order to obtain the information needed to fill various slots. Various other techniques and components can be utilized by device 150 and semantic component 250 in order to obtain interaction data and analyze that data.

The semantic component 250 can evaluate a respect criteria that is associated with the interaction data, where the respect criteria is based on the attention and consideration due to honor each patient, family, community, and society. The respect criteria can includes esteem for family and community, as well as environment. The respect criteria can include full participation by the nurse for persons in their care. Factors such as the nurse acknowledging that each patient has unique life experiences and acknowledging that the patient is the expert "knower" of their own experiences, can be considered in evaluating the respect criteria. Other factors can include the nurse remaining open to learning from the patient about cultural values, practices, beliefs other than their own and honoring the patient, with distinctive values, beliefs and practices.

The semantic component 250 can evaluate a caring criteria that is associated with the interaction data, where the caring criteria is based on nurturing wholeness and well being of patients, families, communities, and societies. The caring criteria can be based on factors such as knowing and understanding the patient's values, interests, preferences and priorities. Other factors can also be used in evaluating the caring criteria such as the being, doing and relating, devotions and commitments of persons, families and communities based on deeply held values and beliefs that direct interests, concerns, preferences, priorities and choices in the patient's life. Day to day living, including health care practices, can be factors in evaluating the caring criteria, as well as hopes, dreams and plans for the future.

The semantic component 250 can evaluate a wholeness criteria that is associated with the interaction data, where the wholeness criteria is based on the patient always being complete as to self, a unity of all aspects of self. The wholeness criteria can include factors such as recognizing that patients by nature are whole and complete as self, including all aspects of self, the entire, total person. Other factors for evaluating the wholeness criteria can include each person being a dynamic and complex unit possessing both uniqueness and attributes in common with others. The well being of a patient can call for the nurse to understand the whole person, not only his or her disease or the limitations of his or her situation, and must come to know the context of his or her life.

The semantic component 250 can evaluate a connection criteria that is associated with the interaction data, where the connection criteria is based on patients, families and communities being joined by shared values and commitments, choices and social structures. The connection criteria can include factors such as each patient being interconnected and interdependent with others in family, community and larger networks and societies. Other factors can include the patient's goals for health and daily health care practices which reflect these connections, as well as networking which reflects and supports family and community values. Additional factors can include each patient, family, community and society being interconnected with the environment, relying on air, food, water and other aspects of the environment for well being.

The semantic component 250 can evaluate an access criteria that is associated with the interaction data, where the access criteria is based on the patient's ability to obtain or make use of needed healthcare services in relationship with nurses and other health care providers. The well being of patients, families and communities can require encounters and continuing relationships with nursing and other providers of health care. Other factors can include the resources and services being culturally and socially acceptable and being available to those in need. Additional factors can include patients and families requiring knowledge of how to approach or enter and take advantage of needed services while having the right to use services for health and well being.

The semantic component 250 can evaluate an essentiality criteria that is associated with the interaction data, where the essentiality criteria is based on nursing and healthcare that is necessary to health and well being, as described by patients, families and communities. One of the factors in evaluating the essentiality criteria is that the patient that is the focus of nursing is the key to defining and understanding essentiality. Other factors include determining whether the nursing adequately listened, heard, understood and communicated what is essential to health of patient, family and community as well as to provide information, explanations and support needed for making decisions regarding health care.

The semantic component 250 can evaluate an empowerment criteria that is associated with the interaction data, where the empowerment criteria is based on the control and power for choice for health and well being experienced by patients, families and communities when choices and care practices are understood, meet their goals for well being and fit within the context of their lives. Empowerment can be experienced when the patient and nurse work together to achieve the healthcare desired within the context of culture and society. The empowerment criteria factors can include recognizing that choices may be made from a range of options for healthcare and caring practices, and the nurse can then assist the patient, family or community in making choices and in developing and sustaining actions to fulfill these choices.

The semantic component 250 can evaluate a community participation criteria that is associated with the interaction data, where the community participation criteria is based on collaboration of various providers and representatives of community services and agencies for addressing concerns of health and well being of patients, families and communities of mutual concern. Collaborative processes can be useful to develop and sustain community partnerships for purposes of promoting health and well being. These processes may be short term, informal, or more formal partnerships and may take various structures. Community processes enable patients to become actively and genuinely involved in defining health issues of concern to them, in making decisions that affect their lives, in forming and implementing policies and developing services to achieve well being. In many instances community representatives lead in making decisions that influence care that is available to patients and families. The patient and family, with the nurse, may identify, utilize or co-create community resources that enhance well being. In these ways, care opportunities are created from the inside out instead of being imposed by a community.

The semantic component 250 can evaluate a intersectoral collaboration criteria that is associated with the interaction data, where the intersectoral collaboration criteria is based on partnerships and organizations among providers and agencies to address particular ongoing concern for health and well being. Partnerships and processes can be developed among health care providers to generate solutions, utilize resources, or to motivate involvement to support and promote well being. Nursing and other providers and service agencies can link to advocate for health and well being of persons and families. Nursing can be active with those in other community services and with colleagues to develop partnerships and services needed to support health of the community and of patients and families within the area. Intersectoral collaboration may also focus on care of the environment for health of populations or groups of persons. Representatives of various agencies can bring their various resources to bear on mutually accepted goals for the community.

In one embodiment, the semantic component 250 of device 150 can evaluate or otherwise view the various criteria for the interaction data described above from the nurse's perspective. The evaluated criteria can provide for ways to view and offer care for the patient, family and community. The patient can be recognized as responsible and accountable for caring for self.

Figure 6:
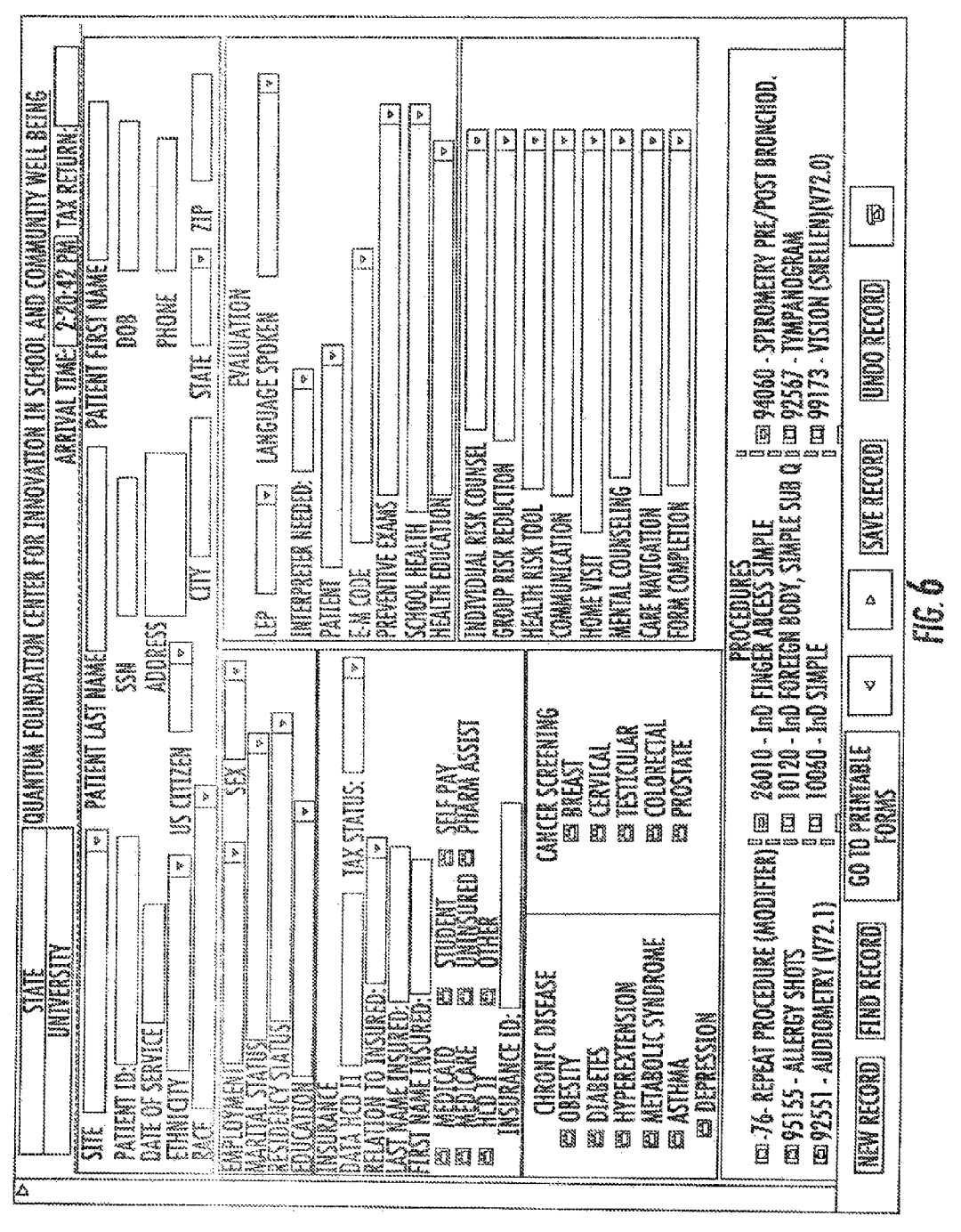

As can be seen in the user interface module 275 of FIG. 5, the interaction data can be captured in a number of different ways including speech, text, and structured input (e.g., drop down menus). Referring additionally to FIG. 6, a graphical user interface in the form of an encounter form can be utilized in combination with the capture of the interaction data. In one embodiment, the device 150 can utilize a direct input technique where the nurse inputs interaction data as it occurs or in temporal proximity thereto, and as he or she deems it necessary for evaluation by the system 100.

In another embodiment, the nurse can input the information subsequent to the interaction, such as in response to prompts provided by the device 150. For example, following the interaction with the patient, the nurse can enter general information such as in the encounter form and then respond to various prompts provided by the device 150. The prompts can be generated based in part on the information retrieved from the encounter form as well as from other medical information associated with the patient, such as retrieved from the medical databases 160. In this example, the device 150 can provide the nurse with feedback as to her interaction and also allow the nurse to gather additional information that may be helpful to assessing the patient.

In yet another embodiment, the device 150 can monitor the interaction between the nurse and patient, such as through recording the discussions, and automatically commence evaluation of the interaction data. For instance, the device 150 can capture the interaction data without intervention of the nurse. In one embodiment, the capturing of the interaction data is not limited to recording discussions and can include capturing video or images of the patient to evaluate facial expressions and so forth, such as through facial recognition and evaluation techniques. In this example, device 150 can further provide prompts for additional information to be input by the nurse, such as the patient's demeanor during particular discussions and so forth.

Figure 7:
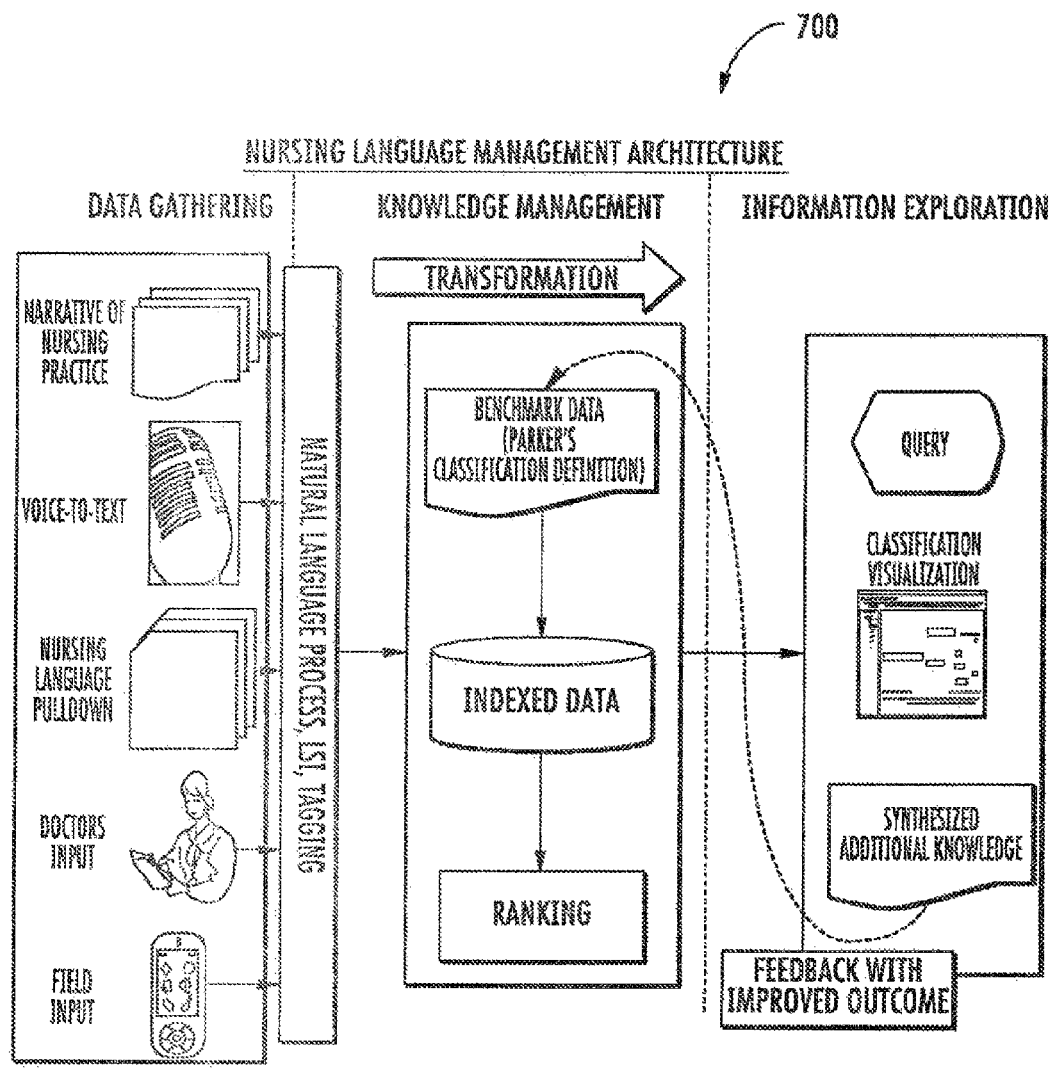
FIG. 7 depicts an exemplary embodiment of an architecture for providing healthcare or wellness, including capturing nursing care practice.

Referring to FIG. 7, another embodiment of an architecture that can be used for capturing and processing interaction data is shown and generally referred to by reference numeral 700. Architecture 700 can utilize a plurality of input techniques in a data gathering module which include voice, pull-down menus, nursing narratives, physician input and remote input. Once the data is gathered, the architecture 700 can employ natural language processing techniques as part of a knowledge management module for analyzing the data, such as NLP, Latent Semantic Indexing (LSI), tagging and/or other artificial intelligence techniques. This module can transform the data such as through ranking and indexing based on various factors, including a library or database of nursing classification definitions or other benchmark comparators. The transformed data can then be provided to an information exploration module to undergo various algorithms and queries in order to utilize the interaction data to better understand the patient's condition and improve the healthcare provided.

In one embodiment, the information exploration module can present a visual depiction of the interaction data captured. For example, the interaction data can be visually presented so that the nurse has a better understanding of one or more of the interaction criteria (such as the caring criteria or the respect criteria). This type of feedback can be used in real-time to assist the nurse in providing improved nursing care to the patient, as well as continuing the interaction with the patient in order to capture interaction data associated with the other interaction criteria.

In one embodiment, the transformed interaction data associated with the patient can be synthesized by the information exploration module and provided back to the database of benchmark comparators. In this example, the benchmark data can be built up as interactions with the patient occur. For instance, the interaction data can be captured based on encounters that occur on numerous different occasions at numerous different facilities for the patient. The encounters can involve the same nurse(s) or different nurse(s). The interaction data can also be based on different medical conditions. Continuing with this example, the benchmark data can be captured for the patient based on a first series of encounters when the patient is hospitalized with a first set of symptoms and complaints. Subsequently, the benchmark data can be updated for the patient based on a second series of encounters when the patient is hospitalized with a second set of symptoms and complaints. The similarities and distinctions between the symptoms and complaints can also be utilized by the exemplary embodiments in evaluating the interaction data. For example, if the patient utilized certain terms to describe his pain during a first series of encounters and asserted that he had pain of ten on a scale of one to ten which turned out to be for a minor injury, then an accuracy prediction can be employed for the patient based on subsequent encounters and his or her use of similar terms to describe the pain.

In another embodiment, the benchmark data that is being feedback from the information exploration module to the knowledge management module can be based on a group of patients rather than limited to a single patient. For example, the benchmark data can be generated based on a group of patients having similar characteristics, such as the type of symptoms, type of complaints, age, gender and so forth.

Figure 9A:
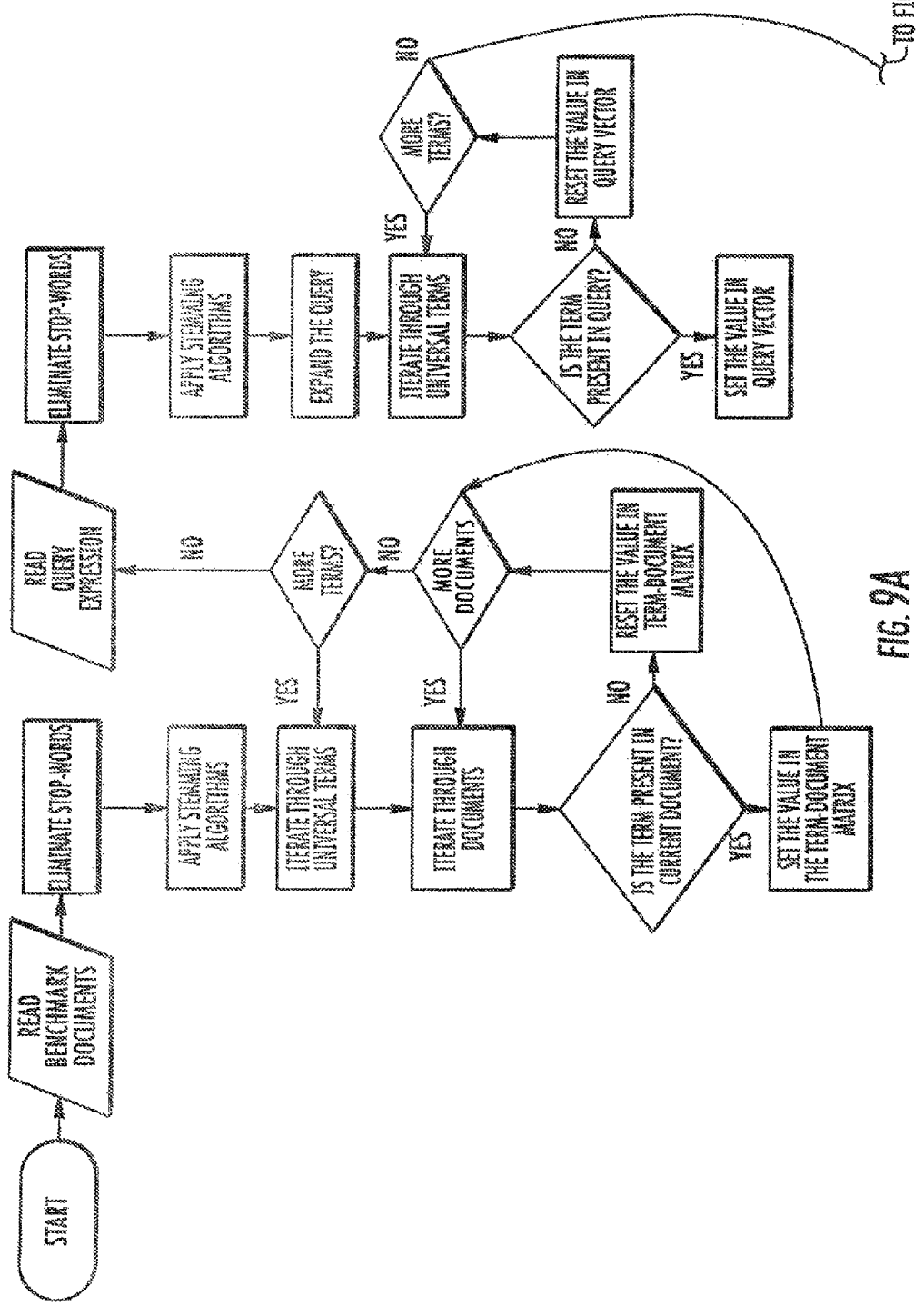
FIGS. 9A and 9B depict an exemplary embodiment of a process flow for one or more of the embodiments of FIGS. 1-8.
Figure 9B:
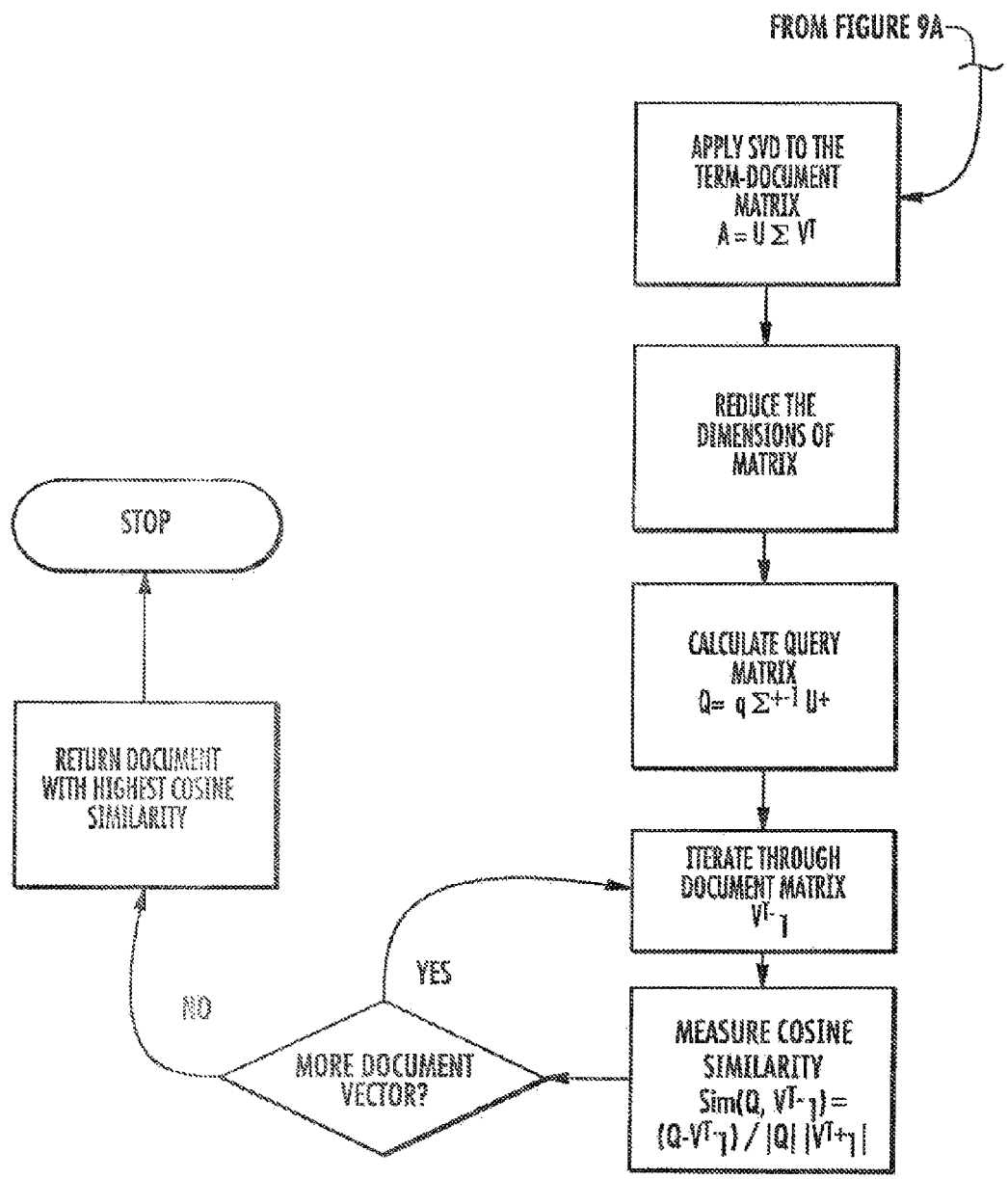

Referring additionally to FIGS. 9A and 9B, a process flow 900 is shown for one exemplary embodiment of evaluating the interaction data. Process 900 can include reading or otherwise accessing the benchmark documents, eliminating stop words, applying stemming algorithms, and iterating through universal terms. Once this evaluation of the captured nursing language terms is performed, then process 900 can generate a term-document matrix and apply a cosine similarity function to determine the highest cosine similarity and therefore perform language comparison.

Figure 11:
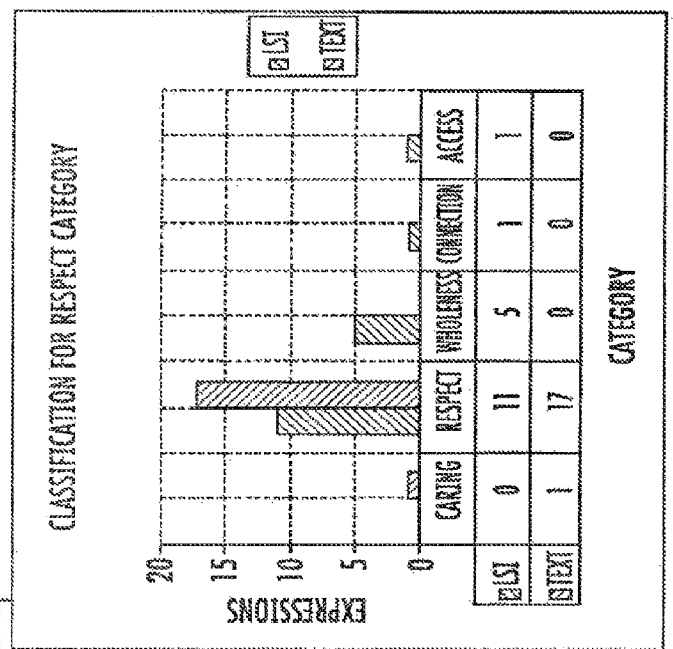
FIG. 11 depicts a graphical representation of additional results obtained using the exemplary embodiments described herein.
Figure 10:
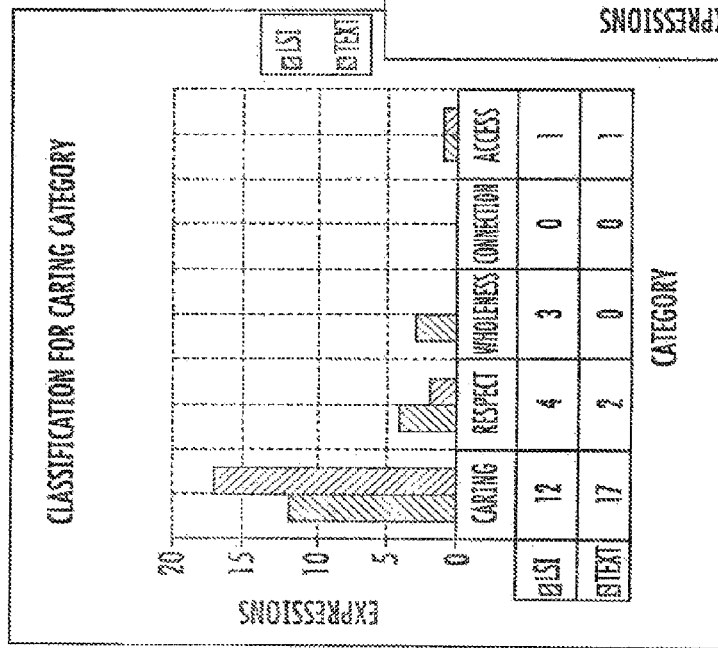
FIG. 10 depicts a graphical representation of results obtained using the exemplary embodiments described herein.
Figure 12:
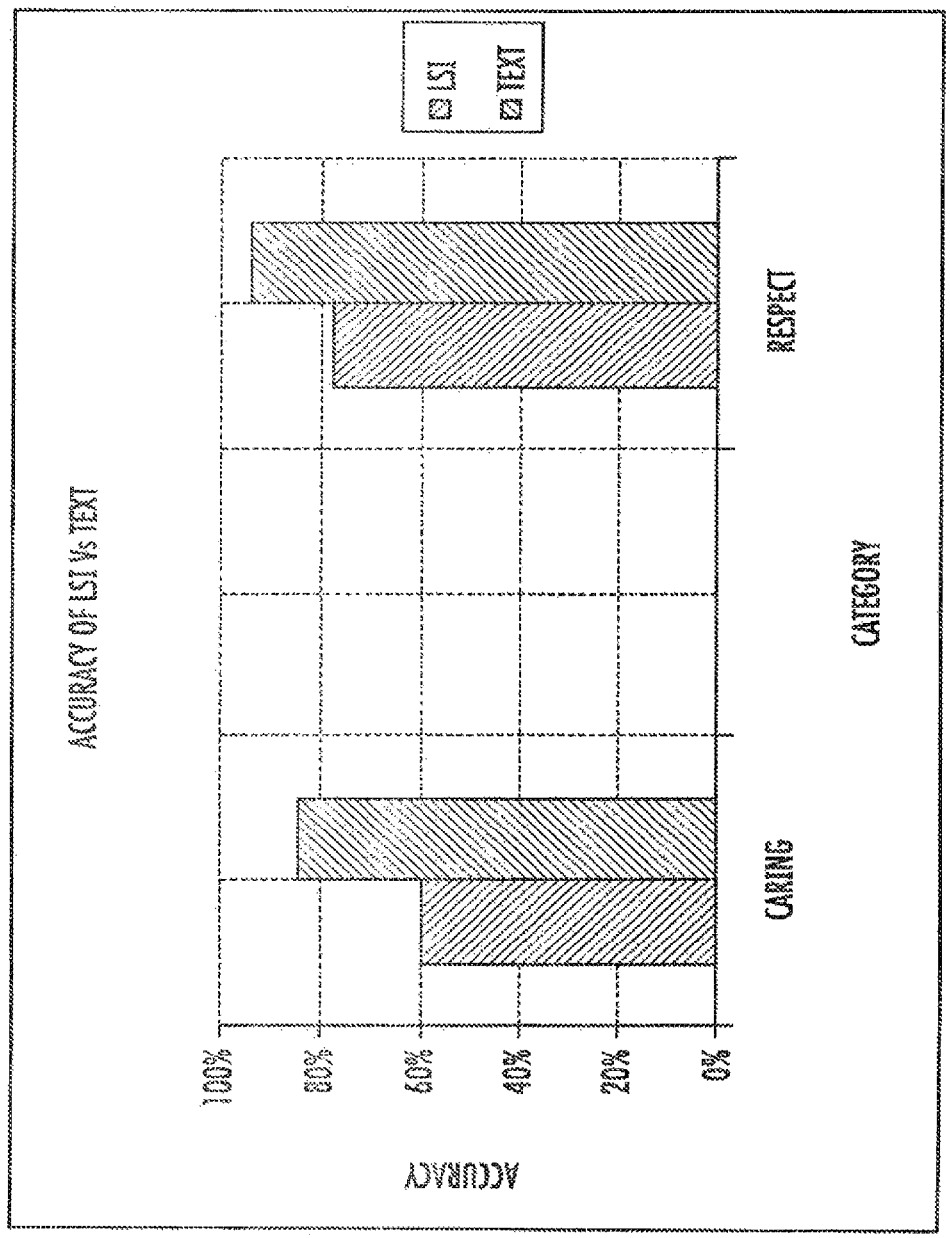
FIG. 12 depicts a graphical representation of additional results obtained using the exemplary embodiments described herein.
Figure 13:
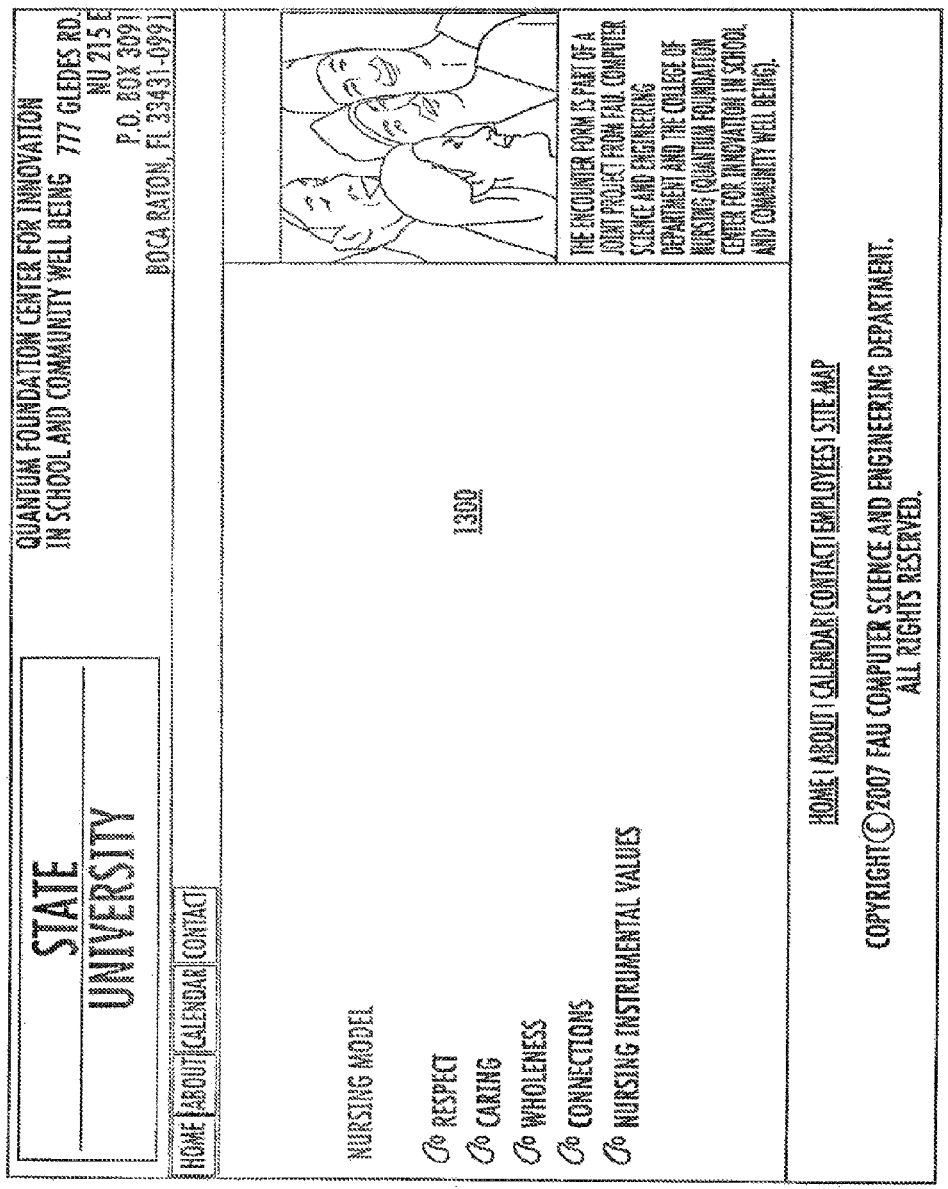
FIG. 13 depicts a graphical user interface for one or more of the embodiments of FIGS. 1-9B.
Figure 15:
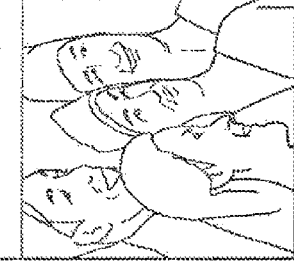
FIG. 15 depicts a graphical user interface for one or more of the embodiments of FIGS. 1-9B.
Figure 16:
FIG. 16 depicts a graphical user interface for one or more of the embodiments of FIGS. 1-9B.
Figure 17:
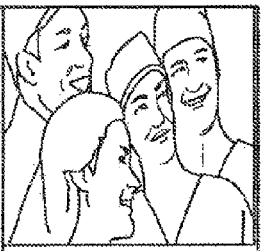
FIG. 17 depicts a graphical user interface for one or more of the embodiments of FIGS. 1-9B.
Figure 18:
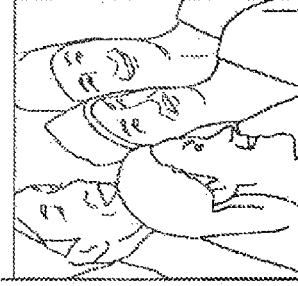
FIG. 18 depicts a graphical user interface for one or more of the embodiments of FIGS. 1-9B.
Figure 19:
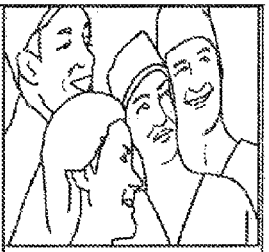
FIG. 19 depicts a graphical user interface for one or more of the embodiments of FIGS. 1-9B.
Figure 20:
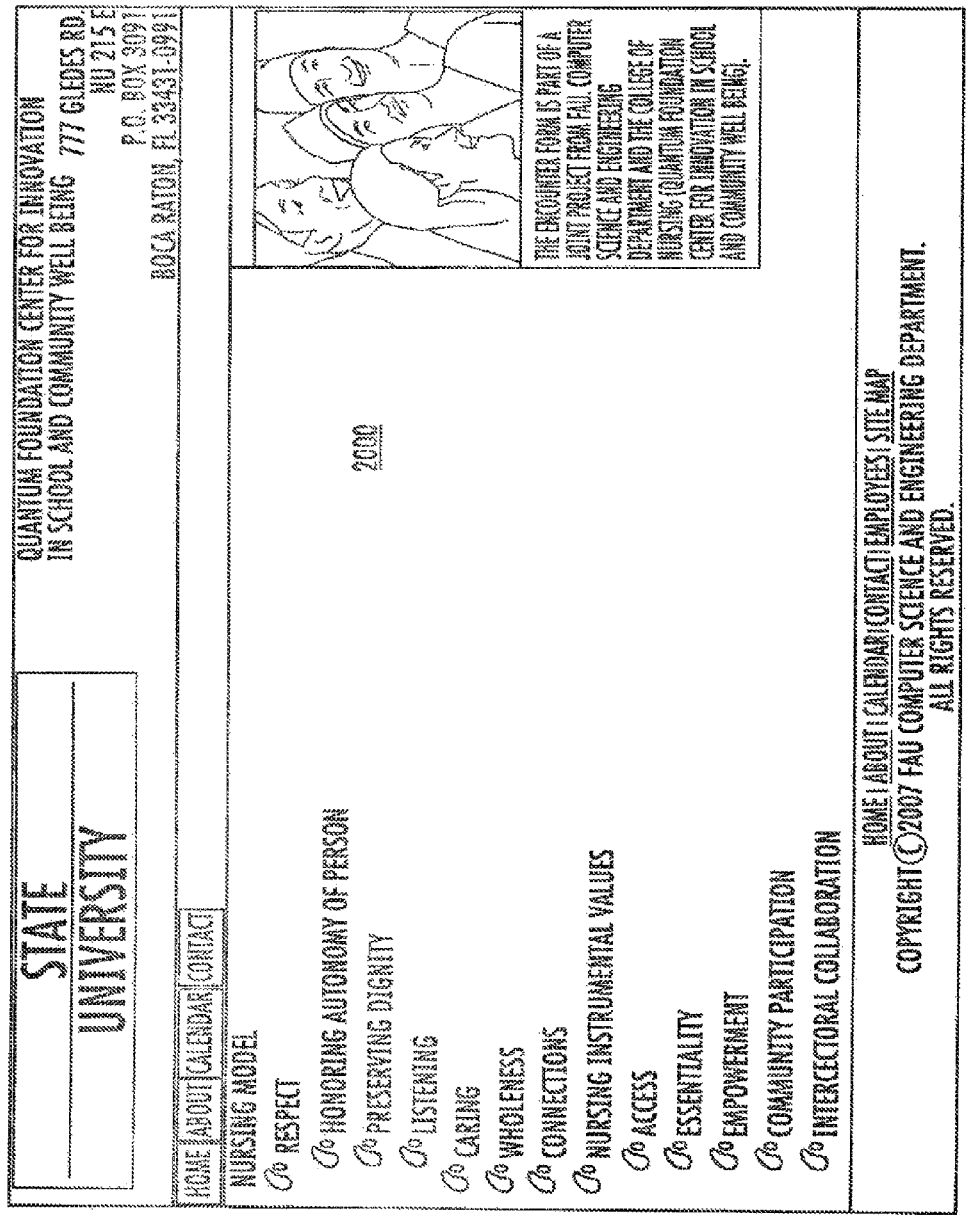
FIG. 20 depicts a graphical user interface for one or more of the embodiments of FIGS. 1-9B.

In one embodiment, the comparisons of the interaction data with the benchmark data can then be indexed and ranked. The rankings associated with the interaction data can be applied to the health risk assessment performed by the syntactic component 225 using the patient's medical records. In one embodiment, the rankings for the interaction data obtained by the semantic component 250 can be utilized as a filter for the health risk assessment results of the syntactic component 225. The resulting filtered information, which now incorporates nursing evaluation of the patient in addition to the static characteristics such as vital signs, test results, patient's asserted complaints and so forth, can be utilized by system 100 to derive a recommendation such as a health care treatment, an alerting message and so forth. Referring additionally to FIGS. 10-12, empirical results for system 100 are shown for the classifications for caring criteria, respect criteria, and the resulting determination of the accuracy of an LSI-based method versus a text based method.

Referring additionally to FIGS. 13-20, a plurality of graphical user interfaces (GUIs) are shown for use with system 100 and/or architecture 700. GUI 1300 can present the nurse with the criteria of respect, caring, wholeness and connections while GUI 1400 allows the nurse to input information associated with the respect criteria, such as honoring the autonomy of the patient. The nurse can also input other information that is not included in a pre-determined selection. GUI 1500 allows the nurse to input information associated with the respect criteria, such as preserving the dignity of the patient. In one embodiment, the system 100 can assess or otherwise evaluate the steps taken by the nurse with respect to the particular criteria, such as whether the patient's dignity has been preserved.

GUI 1600 allows the nurse to input information associated with the respect criteria, such as listening to the patient while GUI 1700 allows the nurse to input information associated with the caring criteria, such as offering presence to the patient. GUI 1800 allows the nurse to input information associated with the wholeness criteria while GUI 1900 allows the nurse to input information associated with the connections criteria. GUI 2000 allows the nurse to input information associated with nursing instrumental value criteria such as access, essentiality, empowerment, community participation, and intersectoral collaboration. As described herein, the exemplary embodiment can utilize this captured interaction data to further assess the health risk derived from the analysis of the medical information or records of the patient and then formulate a healthcare plan or part thereof for the patient.

Upon reviewing the aforementioned embodiments, it would be evident to an artisan with ordinary skill in the art that said embodiments can be modified, reduced, or enhanced without departing from the scope and spirit of the claims described below. For example, various weighting and rankings schemes can be utilized with respect to assessing the interaction data. For instance, the benchmark language library can be used in order to build a model of the patient based on the interaction data. The model can then be subjected to various queries to determine adjustments to be made to the assessed health risks for the patient. As another example, the queries can be used to determine the accuracy of other information that has been used to assess the health risks. The queries can also be utilized to generate historical information to be subsequently applied to the patient or to other patients.

These are but a few examples of modifications that can be applied to the present disclosure without departing from the scope of the claims. Accordingly, the reader is directed to the claims section for a fuller understanding of the breadth and scope of the present disclosure.

One or more of the exemplary embodiments can include a nursing language model software system that is a patient-centered, nursing-oriented health care software system. The system can document caring by a nurse for a particular patient encounter. For example, the system can contain various fields to quantitatively document caring through various aspects such as offering presence, respect, connecting and so forth. This can then be linked to how the health outcome of the patient is influenced by the nurse based on the nurse's knowledge. The system can facilitate understanding and evaluating nurse influence on health outcome of the patient to other health related disciplines including social work and so forth. The system is not intended to be limited to any particular environment and can be utilized in various settings, such as community, rehabilitation, and/or acute care where a nurse provides care to the patient.

One or more of the exemplary embodiments can include an intelligent system, which, through computer aided knowledge discovery, would extract data from a nurse's narrative and integrate into a nursing-oriented electronic healthcare record software. The system can utilize clustering and machine learning algorithms to carry out knowledge extraction through computational intelligence. This serves to recognize the value of caring and time required for nursing practice. It also can have the advantage of supporting nurse satisfaction, recruitment and retention in healthcare agencies.

In one embodiment, the system can present information that allows for the validation of the distinctive contribution of the nursing practice; and the demonstration and measurement of nursing outcomes. In another embodiment, the system can provide continuity of care across healthcare settings, such as between an acute care facility and a rehabilitation facility. The system can also be used to present the quality and cost effectiveness of the healthcare, and in particular the nursing care, as well as improve the allocation and management of resources.

In another embodiment, the system can provide for capturing and communicating of nursing care systematically. The system can integrate nursing information with other aspects of healthcare reporting. For instance, the system can provide for continuity of treatment, particularly where the later treatment (such as in a rehabilitation facility) is primarily nursing care. In another embodiment, the system can improve nursing practice by capturing and assessing expressions of nursing, such as through establishing a database of nursing language that is utilized with natural language software for generating or otherwise adjusting a healthcare model associated with the patient.

One or more of the exemplary embodiments can provide for accountability of nurses for their values, practice and knowledge, including assisting in formalizing nursing practice. For instance, the system can be utilized to provide feedback to the nurse as to best practices. In this example, the system can contribute to the knowledge of the discipline, while also providing for nursing education and training. For instance, patient models can be collectively analyzed to determine best practices associated with particular medical conditions. These best practices can then be communicated to the nurses through training programs and/or in real time, such as during an encounter using a communication device that the nurse has access to and is operably connected with the system.

In one embodiment, the system can replace the ad hoc capturing of fragmented physiological data to the systematic capturing of nursing knowledge. The system can also make implicit information associated with the patient explicit. The system allows for quantifying qualitative data and structuring unstructured data.

One or more of the exemplary embodiments provide a system that allows for facilitating healthcare without the need for nurses to classify the data manually. The system can avoid inconsistency such as different results and different plans of care for different nurses. The system can also avoid ambiguity, such as ambiguous expression which may lead to wrong classification.

The components of system 100 can employ various communication devices for communicating with each other by way of wireless access points and/or wired infrastructure, including servers, network elements and/or a network proxy or web server. The communication devices can be multimedia devices for communicating video, voice, text and/or data. For example, the communication devices can include laptop or desktop computers, cellular phones, PDAs, iPhones, and/or other devices that can communicate one or more of video, voice and data signals. The communication devices can include various components and combinations of components that provide for the above-described communication, as well as other functions, such as, controllers, processors and memory. In one embodiment, the communication devices can communicate in a multimode communication environment that can communicate via a number of modes of communication, including wired and/or wireless communication, as well as pursuant to various protocols.

The system 100 can utilize a packet-switched network, such as an Internet Service Provider (ISP) network, and can be coupled to a network proxy (not shown), a cellular network, a WiFi network, and/or network elements. The ISP network can utilize technology for transporting Internet traffic. Communications can conform to any number of signaling protocols such as a session initiation protocol (SIP), SS7, or a video communications protocol which combines video and voice over a packet-switched network, as well as cryptographic protocols, such as transport layer security (TLS) or secure sockets layer (SSL), to provide secure communications for data transfers.

A network proxy (not shown) can be utilized which comprises a communications interface that utilizes common technology for communicating over an IP interface with device 150, communication devices, the network, the cellular network, and/or the WiFi network. By way of the communications interface, the network proxy can direct by common means any of the foregoing network elements to establish packet switched data, voice, and/or video connections between communication devices distributed throughout the system 100. The network proxy can include memory (such as a high capacity storage medium), and a controller that makes use of computing technology such as a desktop computer, or scalable server for controlling operations of the network proxy. The network proxy can operate as an IP Multimedia Subsystem (IMS) conforming in part to protocols defined by standards bodies such as 3GPP (Third Generation Partnership Protocol) and beyond.

The present disclosure contemplates the use of a machine in the form of a computer system within which a set of instructions, when executed, may cause the machine to perform anyone or more of the methodologies discussed above. In some embodiments, the machine can operate as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine can comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure can include broadly any electronic device that provides voice, video or data communication. Further, while a single machine is illustrated, the term "machine" shall also be taken to include any collection of machines that individually or jointly execute a set (or multiple sets) of instructions to perform anyone or more of the methodologies discussed herein.

The computer system can include a processor (e.g., a central processing unit (CPU), a graphics processing unit (GPU, or both), a main memory and a static memory, which communicate with each other via a bus. The computer system can further include a video display unit (e.g., a liquid crystal display (LCD), a flat panel, a solid state display, or a cathode ray tube (CRT)). The computer system can include an input device (e.g., a keyboard), a cursor control device (e.g., a mouse), a mass storage medium, a signal generation device (e.g., a speaker or remote control) and a network interface device. [0083] The mass storage medium can include a computer-readable storage medium on which is stored one or more sets of instructions (e.g., software) embodying anyone or more of the methodologies or functions described herein, including those methods illustrated above. The computer-readable storage medium can be an electromechanical medium such as a common disk drive, or a mass storage medium with no moving parts such as Flash or like non-volatile memories. The instructions can also reside, completely or at least partially, within the main memory, the static memory, and/or within the processor during execution thereof by the computer system. The main memory and the processor also may constitute computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on one or more computer processors. Furthermore, software implementations can include, but not limited to, distributed processing or component/object distributed processing, parallel processing, or virtual machine processing can also be constructed to implement the methods described herein.

The present disclosure also contemplates a machine readable medium containing instructions, or that which receives and executes instructions from a propagated signal so that a device connected to a network environment can send or receive voice, video or data, and to communicate over the network using the instructions. The instructions can further be transmitted or received over a network via the network interface device. While the computer-readable storage medium is described in an exemplary embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform anyone or more of the methodologies of the present disclosure. The term "computer-readable storage medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape. Accordingly, the disclosure is considered to include anyone or more of a computer-readable storage medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72 (b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A non-transitory computer-readable storage medium for managing healthcare, the storage medium being embedded with computer instructions for:
   retrieving medical records corresponding to a patient;
   analyzing the medical records to assess a health risk for the patient;
   receiving interaction data, wherein the interaction data is derived, at least in part, from a recording of a live encounter between the patient and a nurse, wherein the interaction data comprises the patient's expression of needs with respect to at least human interaction and the nurse's expression of caring for the patient with respect to the patient's expression of needs;
   comparing the interaction data to interaction criteria; and
   determining a healthcare plan for the patient based at least in part on the assessed health risk and the comparison of the interaction data to the interaction criteria.

2. The storage medium of claim 1, further comprising computer instructions for assembling the interaction data,
   wherein the assembling comprising receiving a speech input from the recording, converting the speech input into text, and adding the text to the interaction data, and
   wherein the comparing comprises applying a natural language process to classify and compare the interaction data to the interaction criteria.

3. The storage medium of claim 1, wherein the interaction criteria comprises at least one of a respect criteria, a caring criteria, a wholeness criteria and a connection criteria.

4. The storage medium of claim 1, wherein the interaction criteria is independent of vital signs, test results and asserted complaints of the patient.

5. The storage medium of claim 1, further comprising computer instructions for adjusting a library of nursing benchmark language based at least in part on the received interaction data.

6. The storage medium of claim 1, further comprising computer instructions for receiving the interaction data from a selection of pre-determined options via a user interface.

7. The storage medium of claim 1, further comprising automatically deriving the data from the recording without intervention of the nurse.

8. A management system comprising:
   a processor;
   a storage medium comprising instructions for causing the processor to:
      retrieve records corresponding to an individual and analyze the records to assess a condition for the individual;
      capture interaction data, wherein the interaction data is derived, at least on part, from a recording of a live encounter between the individual and a service provider, wherein the interaction data comprises the individual's expression of needs with respect to at least human interaction and the service provider's expression of caring for the individual with respect to the individual's expression of needs; and
      compare the interaction data to interaction criteria, wherein an action plan for the individual is generated based at least in part on the assessed condition and the comparison of the interaction data to the interaction criteria.

9. The system of claim 8, wherein the service provider is a nurse and further comprising a library of nursing benchmark language that is adjusted based at least in part on the received interaction data for the individual.

10. The system of claim 9, wherein the library is adjusted based on interaction data associated with one or more other individuals.

11. The system of claim 8, wherein the service provider is a nurse, and wherein the interaction criteria comprises at least one of a respect criteria, a caring criteria, a wholeness criteria and a connection criteria.

12. The system of claim 8, the storage medium further comprising instructions for causing the processor to present feedback to the service provider based on the interaction data.

13. The system of claim 8, wherein the storage medium further comprising instructions for causing the process to receive a speech input from the recording, convert the speech input into text, and add the text to the interaction data, and
   wherein the comparing comprises applying a natural language process to classify and compare the interaction data to the interaction criteria.

14. The system of claim 8, wherein the interaction data is captured by a remote portable device.

15. A method for managing healthcare, the method comprising:
   receiving interaction data at a processor, the interaction data being derived, at least in part, from a recording of with an encounter between a patient and a nurse, wherein the interaction data comprises the patient's expression of needs with respect to human interaction and the nurse's expression of caring for the patient with respect to the patient's expression of needs;
   comparing the interaction data to interaction criteria by applying a natural language process of the processor; and determining a healthcare plan for the patient based at least in part on the comparison of the interaction data to the interaction criteria using the processor.

16. The method of claim 15, further comprising:
accessing stored medical information corresponding to the patient;
analyzing the medical information to assess a health risk for the patient using the processor; and
determining a healthcare plan for the patient based at least in part on the assessed health risk and the comparison of the interaction data to the interaction criteria using the processor.

17. The method of claim 16, further comprising assembling the interaction data,
wherein the assembling comprises receiving the interaction data from a speech input of the recording, converting the speech input into text, and adding the text to the interaction data.

18. The method of claim 15, wherein the interaction criteria comprises at least one of a respect criteria, a caring criteria, a wholeness criteria and a connection criteria.

19. The method of claim 15, wherein the interaction criteria is independent of vital signs, test results and asserted complaints of the patient.

20. The method of claim 15, further comprising adjusting a library of nursing benchmark language based at least in part on the received interaction data.

21. The method of claim 15, wherein the interaction data is derived by the processor.

* * * * *